United States Patent [19]
Hillstead et al.

[11] Patent Number: 5,755,702
[45] Date of Patent: May 26, 1998

[54] ADJUSTABLE ANGULAR SHEATH INTRODUCER

[75] Inventors: Richard A. Hillstead, Duluth; Stephanie Danielle Teemer, Decatur; Sherri Lynn Padgett, Dacula, all of Ga.

[73] Assignee: Novoste Corporation, Norcross, Ga.

[21] Appl. No.: 635,496

[22] Filed: Apr. 22, 1996

Related U.S. Application Data

[63] Continuation-in-part of Ser. No. 230,614, Apr. 21, 1994, Pat. No. 5,509,908, and Ser. No. 24,444, Jun. 14, 1994, Pat. No. Des. 374,076.

[51] Int. Cl.⁶ ............................................. A61M 5/00
[52] U.S. Cl. .................. 604/264; 604/282; 604/169; 604/167
[58] Field of Search .................. 604/164, 167, 604/169, 171, 264, 284

[56] References Cited

U.S. PATENT DOCUMENTS

| | | | |
|---|---|---|---|
| 4,013,310 | 3/1977 | Dye | 285/110 |
| 4,323,065 | 4/1982 | Kling | 128/214 |
| 5,330,449 | 7/1994 | Prichard | 604/282 |

FOREIGN PATENT DOCUMENTS

WO 94/01161  1/1994  WIPO.

*Primary Examiner*—Michael Powell Buiz
*Assistant Examiner*—N. Kent Gring
*Attorney, Agent, or Firm*—Bernstein & Associates

[57] ABSTRACT

A sheath introducer for a catheterization or similar procedure comprises a main body having an exterior tapered sidewall, an interior lumen, a beveled top surface and an annular boss extending from the top surface; a rotating section having an exterior sidewall, an interior lumen, a beveled bottom surface having a recessed portion dimensioned so as to be received within the main body annular boss, and a top surface having an annular shoulder extending therefrom creating a recess; a cannula extending from the bottom end of the main body; and, a hemostatic valve having an access port and a fluid tight slit opening and seated within the upper portion and maintained by a cap, the valve being maintained within the rotating section recess and preferably slightly compressed when the rotating section and main body are assembled. When assembled, the rotating section can rotate up to approximately 180°, affording approximately a 45° angle between the main body lumen and the rotating section lumen while maintaining an open passageway for insertion of catheters or other objects. Optionally, an angled sideport in fluid communication with the main body lumen extends from the main body.

27 Claims, 18 Drawing Sheets

ADJUSTABLE ANGULAR SHEATH INTRODUCER

CROSS-REFERENCE TO RELATED APPLICATIONS

The present invention is a continuation-in-part of applications U.S. Ser. No. 08/230,614, Apr. 21, 1994 now U.S. Pat. No. 5,509,908, and Ser. No. 29/024,444 filed Jun. 14, 1994 now Design Pat. No. D.374,076. The disclosures of both applications are incorporated by reference herein.

FIELD OF THE INVENTION

The present invention relates to a hemostatic sheath introducer, and more particularly to a sheath introducer that can slidingly receive catheters or other similar devices after being inserted into a vessel while providing an improved angle for inserting and manipulating a catheter.

BACKGROUND OF THE ART

Hemostatic sheath introducers are well known in the art as devices for facilitating insertion, removal and manipulation of stents, catheters or like devices into a vein or artery. A procedure has been developed using devices called Transjugular Intrahepatic Portal-systemic Shunts ("TIPS"), in which a catheter is inserted into the jugular vein via a sheath introducer. A sheath introducer is an access device comprising a cannula with fluid barrier valve and an access port. The cannula portion is inserted into a patient's blood vessel, typically an artery, and a number of different devices are insertable into the sheath introducer and into the vessel with an objective being to cause minimal trauma to the vessel and surrounding area.

Intrahepatic portal-systemic shunts are artificial fistulas between branches of the portal vein and the systemic circulation in the substance of the liver. The insertion and deployment of such shunts are among the most complex procedures in interventional medicine. During the procedure a number of catheters or similar devices must be inserted into a blood vessel via the sheath introducer. Currently available sheath introducers, such as that described in U.S. Pat. No. 4,000,739, issued to Stevens, and its progeny, utilize a straight bodied sheath introducer and are normally used for insertion into certain areas of the body. Insertion of a cannula into the jugular vein involves a less flexible site because the curved jaw and neck area provide awkward placement of a sheath introducer relative to the patient's body.

The sheath introducer of Stevens utilizes a straight body and co-axially aligned cannula, with a tapering body portion integrating with the cannula. Because the cannula is mounted in the center of the bottom of the body, this sheath introducer design has a disadvantage that when it is inserted into the vessel the body of the introducer can lift the cannula away from the surface of skin area, possibly causing stress and trauma to the vessel underneath and kinking the introducer cannula. Additionally, the access port is co-axially aligned with the cannula requiring insertion of catheters to be made substantially horizontal to the skin and a catheter may be difficult to insert where the cannula is inserted near the uneven topography of the jaw and neck region. It would be desirable to have a cannula that would angle away from the skin to permit more facile insertion of a catheter and reduce pulling and trauma to the vessel during insertion. It would also be desirable to have a cannula that extended eccentrically from the body of the introducer to minimize bending of the cannula with respect to the vessel and to prevent or reduce the likelihood of kinking the cannula.

Since the development of the original embodiments disclosed in the parent copending application, it has been found that it would be desirable to have a sheath introducer which would have an adjustable angle. Practitioners may want to introduce catheters or other tubing into the introducer while the introducer is at a 0° straight orientation, but, the patient comfort may be optimized by having the introducer adjusted to a different angle. Such need inspired the embodiments disclosed in the present invention.

SUMMARY OF THE INVENTION

The present invention provides a hemostatic sheath introducer suitable for TIPS and other catheterization procedures where an adjustable angled access port is useful.

Generally described, the present invention provides, in a first preferred embodiment, a sheath introducer for a catheterization or similar procedure comprising a main body having an exterior tapered sidewall, an interior lumen, a beveled top surface and an annular boss extending from the top surface; a rotating section having an exterior sidewall, an interior lumen, a beveled bottom surface having a recessed portion dimensioned so as to be received within the main body annular boss, and a top surface having an annular shoulder extending therefrom creating a recess; a cannula extending from the bottom end of the main body; and, a hemostatic valve having an access port and a fluid tight slit opening and seated within the upper portion and maintained by a cap, the valve being maintained within the rotating section recess and preferably slightly compressed when the rotating section and main body are assembled. When assembled, the rotating section can rotate up to approximately 180°, affording approximately a 45° angle between the main body lumen and the rotating section lumen while maintaining an open passageway for insertion of catheters or other objects. Optionally, an angled sideport in fluid communication with the main body lumen extends from the main body.

In a variation of the first preferred embodiment, the main body lumen has an upper portion that angles perpendicularly toward the top surface boss and the rotating section lumen has a lower portion that angles perpendicularly toward the bottom recess. When assembled and rotated, the main body lumen and rotating section lumen maintain an open, circular cross section passageway to facilitate introduction of catheters or other objects in the introducer. The rotation of the rotating section, for both the variation and the first embodiment, permit a user to insert the introducer into the patient's vessel and introduce cathethers or other objects while the introducer is in the unrotated position, and then rotate the rotating section to create greater access to the access port and to improve patient comfort.

The rotating section preferably has a knurled surface so that a user can grip the section easier when rotating and manipulating the access port. Optionally, the main body can have a series of indentations spaced partially around the annular raised boss and a semi-spherical protrusion extending from the rotating section annular recess. When the two parts are mated and rotated, a series of detent stops is created.

A second preferred embodiment provides a hemostatic sheath introducer, comprising:

(a) a generally cylindrically shaped main body having a main axis and comprising an exterior sidewall, having a front portion, a rear portion, a left side portion and a right side portion, the rear portion extending upward higher than the front portion, the exterior sidewall having a taper thereto, a left bracket extending from the left side portion, the left bracket having an aperture defined therein, a right bracket extending from the right side portion, the right bracket having an aperture defined therein, a bottom end, and a first lumen extending therethrough, the lumen having a lower parallel wall portion, a middle reverse tapered portion, an upper curved portion, the curve having a radius of curvature Rm;

(b) a pivoting section comprising an exterior wall having front, rear, left side and right side portions, a lower portion which is curved and having a radius of curvature Rp, the radius Rp being substantially similar to the radius Rm, an upper surface, a second lumen defined therein, the second lumen having a substantially straight rear wall, a front wall that is angled outward toward the exterior wall, a left pintle extending from the pivoting section left side portion, a right pintle extending from the pivoting section right side portion, the left pintle being pivotably receivable within the left bracket aperture and the right pintle being pivotably receivable within the right bracket aperture;

(c) an access port being attachable to the rotating section and comprising a luer fitting portion having an interior luer taper defining a third lumen and an exterior luer fitting, a sealing portion comprising an annular shoulder portion having an exterior dimension generally similar to the exterior dimension of the rotating section upper end, and a recessed portion;

(d) an elastomeric valve having an opening defined therein adapted for receiving an elongated member in a slidingly sealable relationship, the valve being receivable within the recessed portion of the access port and maintained in place thereby; and, (e) a cannula extending from the bottom end of the main body and comprising a proximal end extending from the main body bottom, a distal end, and a fourth lumen extending therethrough being in fluid communication with the first lumen, whereby the pivoting section can pivot on the left and right pintles within the left and right brackets, respectively, while maintaining an open passageway through the introducer.

Optionally, a series of indentations can be formed in the left (or right) side of the pivoting section, just above the left pintle. A semi-spherical protrusion can extend from the inside portion of the left bracket. When the parts are mated, a series of detents are created so that when the pivoting section is pivoted, there are stops of movement.

Accordingly, it is a principal object of the present invention to provide a hemostatic; sheath introducer that affords increased access to the access port.

It is a further object of the present invention to provide a hemostatic sheath introducer that reduces trauma to the skin and vessel.

It is another object of the present invention to provide a hemostatic sheath introducer that has a tapered main body so that the cannula lays flatter with respect skin when in an inserted position.

It is still a further object of the present invention to provide a hemostatic sheath introducer that reduces the likelihood of kinking the cannula during catheter manipulation.

It is yet another object of the present invention to provide a sheath introducer that allows for adjustable angles.

Other objects, features, and advantages of the present invention will become apparent upon reading the following detailed description of embodiments of the invention, when taken in conjunction with the accompanying drawings and the appended claims.

BRIEF DESCRIPTION OF THE DRAWINGS

The invention is illustrated in the drawings in which like reference characters designate the same or similar parts throughout the figures of which.

DESCRIPTION OF THE PREFERRED EMBODIMENTS

Figures 1, 2:
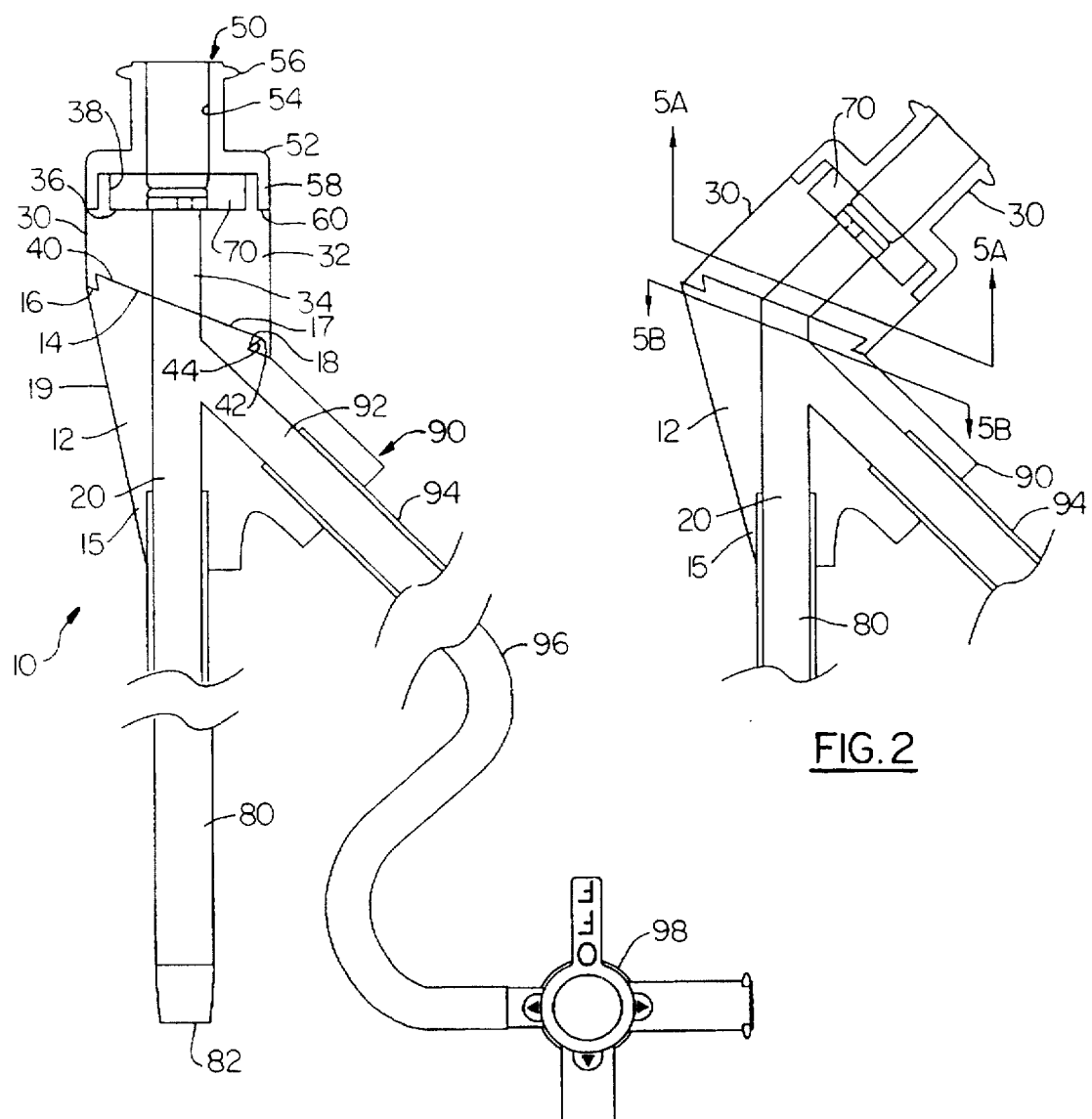
FIG. 1 is a side view of a first preferred embodiment of the sheath introducer of the present invention.
FIG. 2 is a side view of the sheath introducer of FIG. 1 when the rotating section is rotated to an angle of approximately 45°.

FIGS. 1–5 show a sheath introducer 10 according to a first preferred embodiment in which a generally cylindrical main body portion 12 has a top end 14 and a bottom end 15. The top end terminates in a beveled top surface 16. The top surface 16 contains a raised annular flange 17, which preferably has a beveled undercut, indicated at 18. The main body has an external sidewall 19. The main body 12 contains a lumen 20.

Figure 5A:
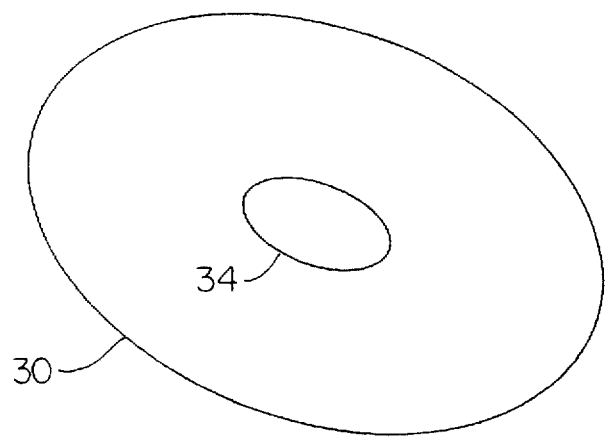
FIG. 5A is a bottom view taken along lines 5A—5A of FIG. 2.
Figure 5B:
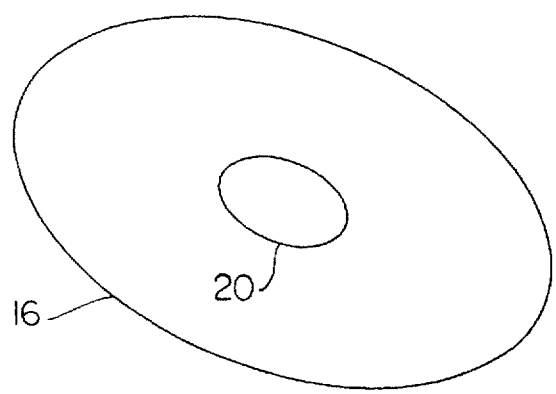
FIG. 5B is a top view taken along lines 5B—5B of FIG. 2.

A rotating, section 30 has a generally cylindrical shape with an exterior sidewall 32 dimension approximating that of the main body 12, and has a lumen 34 extending therethrough in fluid communication with the lumen 20. A top end 36 comprises a generally horizontal (with respect to the sidewall 32) surface having an annular raised boss 38 extending therefrom. The rotating section 30 also has a beveled bottom end 40 having a recessed annular groove 42 defined therein, the groove 42 having a beveled interior sidewall 44 capable of mating rotational engagement with the annular flange 17. The lumen 20 and 34 are in general alignment, both in the rotated and unrotated positions. FIG. 5A shows a cross-section of the top surface 16 of the main body 12 and FIG. 5B shows a cross section the bottom end 40 of the rotating section 30.

An access port cap 50 has an annular body portion 52 having an interior luer tapered lumen 54, an exterior luer fitting 56, and an annular shoulder portion 58 terminating in a downward depending annular rim 60. The rim 60 is sized to be fitted over the rotating section boss 38.

Figure 3:
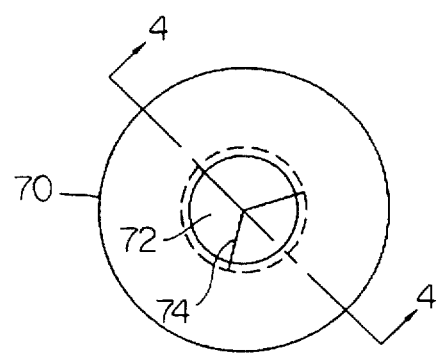
FIG. 3 is a top view of the valve.
Figure 4:
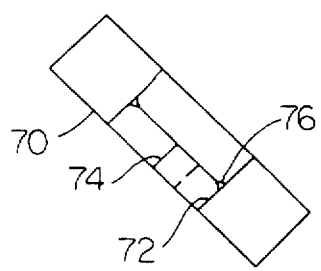
FIG. 4 is a side cutaway view of the valve.

An elastomeric unitary disc-shaped hemostatic valve 70 is seated within the depression created by the raised boss 38 and rests on the rotating section top end 36. The valve 70 comprises a centrally positioned access port aperture 72 extending partially within the valve 70, and a Y-slit 74, as shown in FIGS. 3 and 4. Preferably, a beveled inward-protruding lip 76 extends annularly in the aperture 72, which acts as an additional seal, enhancing the ability of the valve 70 to maintain hemostasis while catheters are being inserted, removed or maintained within the sheath introducer 10. The Y-slit 74 is aligned axially with the aperture 72 and permits entry of a catheter or similar device into the lumen 20 through the aperture 72 and forms a fluid-tight seal when no catheter is present and also when a catheter is inserted into the slit 74. The slit 74 also aligns the catheter for reception within the lumen 20.

A cannula 80 extends from the bottom end 15 and is in fluid communication with the lumen 20. The rear of sidewall 19 is tapered toward the cannula 80 to minimize the distance between the cannula 80 and the rear of the sidewall 19. The purpose of the offset cannula 80 is to maintain a closer alignment with and proximity to the skin and the main body after positioning. The distal end 82 of the cannula 80 is tapered slightly for easier introduction into a vessel and to adhere closely to the exterior surface of a vessel dilator.

Figure 6:
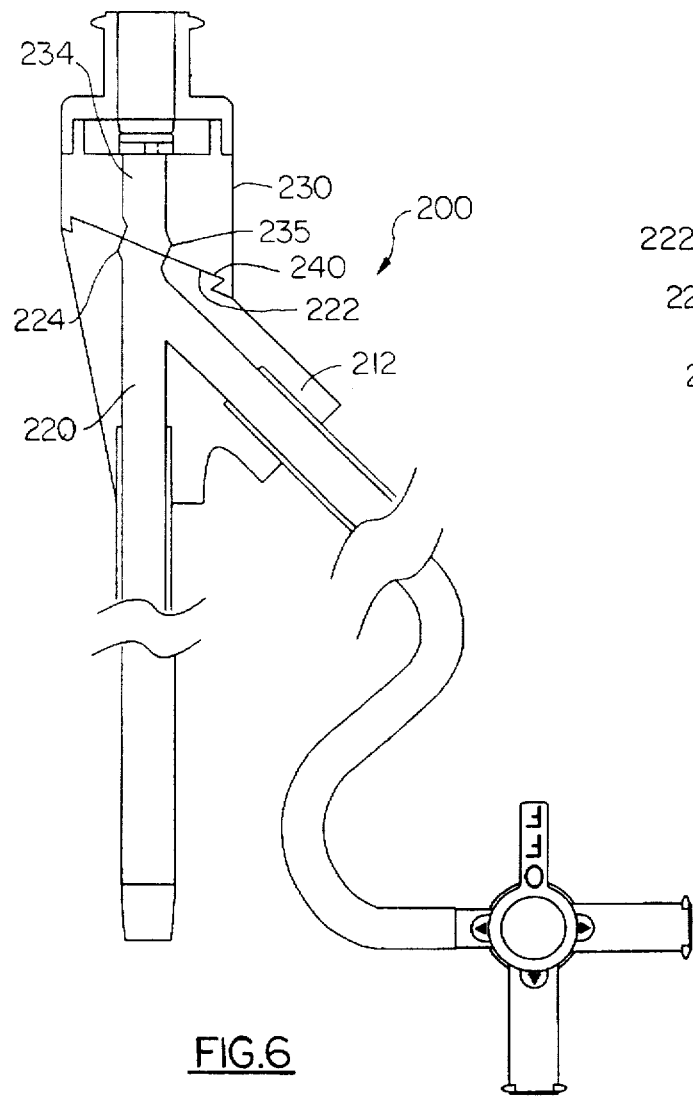
FIG. 6 is a side view of an alternative to the first preferred embodiment of the sheath introducer of the present invention
Figure 7:
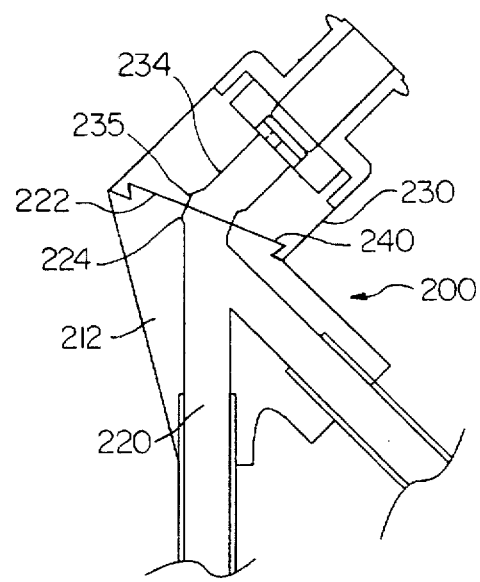
FIG. 7 is a side view of the sheath introducer of FIG. 6 when the rotating section is rotated to an angle of approximately 45°.

An optional, though preferable, sideport 90 extends from the sidewall 19 and has a lumen 92, which is in fluid communication with the lumen 20. The sideport 90 is preferably angled downward at an acute angle toward the cannula 80 so as to prevent any tubing from possibly interfering with insertion operations at the access point cap 50. Alternatively, the sideport 90 can be perpendicular to the cannula 80 or at other angles. A hollow boss 94 further defining the lumen 92 extends from the sideport 90 and connects to a sideport tubing 96, which is connectable to a conventional stopcock 98 or other device. Optionally, as shown in FIGS. 6 and 7 of the co-pending parent application described above, the boss 94 is rotated about 90° (although any suitable angle will suffice) in order to be orthogonal with respect to the cannula 80 and the top 14. It is also possible to eliminate the sideport 90 altogether, if desired. The sideport 90 is useful as a fluid introduction or removal site, when the access port cap 50 is occupied by a catheter or the like. Fluids such as heparin or other clot-preventing solutions can be conveniently introduced via the stopcock 98 into the lumen 20. Also, fluids, including air and air bubbles, can be removed from the introducer 10 by attaching a syringe to the stopcock 90 and withdrawing the plunger.

The main body 12, rotating section 30, cap 50 and cannula 80 are preferably made of any of a number of suitable rigid, biocompatible and cleanable materials, such as high density polyethylene.

A conventional straight dilator 100 (not shown), or an angled one similar to the dilator disclosed in the co-pending parent application described above can be used or one can be adapted for use with the present invention.

In manufacture of the present invention, the parts are molded or otherwise formed by typical techniques and processes known to those skilled in the art. Preferably, the main body 12 and cannula 80 (and sideport 90, if present), the rotating section, and the access port cap 50 are separate pieces, as is the valve 70. To assemble the sheath introducer 10, a valve 70 is placed in the depression created by the annular boss 38. The access port cap 50 is fitted over the boss 38 so that the valve 70 is maintained in position between the rotating section 30 and the access port cap 50 by a slight compressive force. The access port cap 50 and the rotating section 30 are bonded together, such as by ultraviolet curing, gluing, sonic welding, solvent bonding, or other techniques known to those skilled in the art. The rotating section 30 is then snap fitted onto the main body 12 with the beveled sidewall 44 preventing removal of the rotating section 30 from the main body 12. It is also possible to change the order of assembly depending on the manufacturing and assembly processes used.

The sheath introducer 10 of the present invention is optimally used in a TIPS procedure although other catheterization procedures can employ the invention. Such procedures have been described in the literature and are well known in the art. Briefly, however, a blood vessel (such as the jugular) is located by palpating the skin above the desired vessel. A needle is inserted into the vessel. A guidewire is introduced through the needle and into the vessel. The needle is then removed leaving the guidewire in place. A vessel dilator (not shown) with a tapered end slides into a sheath introducer 10 via the aperture 72 and both advance over the wire. The dilator 100 and sheath introducer 10 are then inserted into the vessel. The vessel dilator 100 and wire are then removed leaving the cannula 80 of the sheath introducer 10 remaining in the vessel. When rotated the access port cap 50 is at an angle with respect to the cannula 80, thereby increasing and improving access to the access port cap 50.

The rotating section 30 can be rotated with respect to the main body 12 by grasping the rotating section 30 with thumb and forefinger and twisting. Optionally, the rotating section can have a number of knurls 102, ridges, grooves, tabs, bumps, or other protrusions or surfaces (not shown) attached to or formed therewith which improve gripping the sidewall 32, particularly with a gloved, possibly wet, hand.

While the sheath introducer 10 of the present invention is maintained at the entry site, other objects may be inserted and withdrawn from the access port cap 50, such as, but not limited to, stents, catheters, shunts, needles, syringes, and the like. The introducer 10 of the present invention permits easier insertion of objects into the aperture 72 because the aperture 72 can be angled away from the skin and the neck area or other areas of the body which may hinder insertion. The present invention also improves catheter manipulation, patient comfort and reduces the likelihood of cannula damage or kinking. The tapered rear portion of the sidewall 19 reduces lifting of the skin and vessel away from the body. The optional angled and/or rotated sideport 90 permits unobstructed access to the access port cap 50.

The variable adjustability of the angle creates greater control by the technician depending on the insertion site and surrounding topography.

Figure 8:
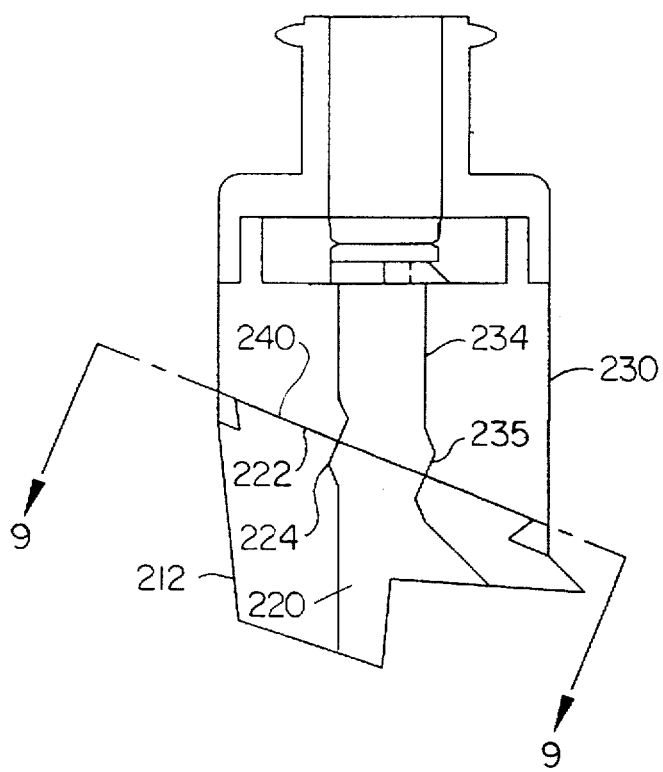
FIG. 8 is a side cutaway detail view of the main body and the rotating section of the introducer of FIG. 6.

In an alternative embodiment of the first preferred embodiment, FIGS. 6–9 show an introducer 200, which has an offset lumen. Unless otherwise described, similar parts are the same as in the first preferred embodiment. The main body 212 has a lumen 220 terminating at a beveled top surface 222. The lumen 220 has an upper offset portion 224, as shown in FIG. 8, whereby the angle of the lumen portion 224 is perpendicular to the surface 222. A rotating section 230 has a lumen 234 having a lower portion 235, which is offset to be perpendicular to a beveled bottom end 240. The lumen portions 224 and 235 therefore are aligned in the unrotated position, shown in FIG. 6 and 8, as well as in the rotated position, shown in FIG. 7.

Figure 9:
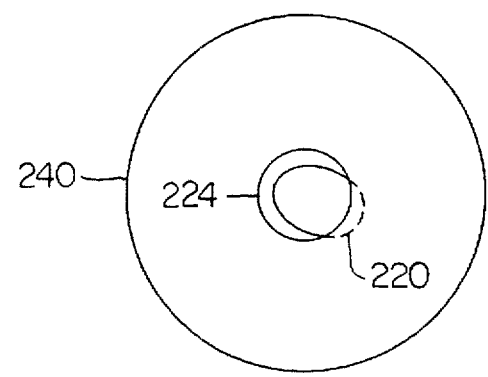
FIG. 9 is a bottom view of the rotating section taken along lines 9—9 of FIG. 8.

FIG. 9 shows a detailed cross section of the lumen portions 224 and 235, with the lumen portion 224 being shown in phantom. The substantial overlap maintains a circular opening in both the rotated and unrotated position, even though the main portion of both lumens 220 and 234 are nonparallel in the rotated position and would otherwise present an oval opening. Thus, this embodiment provides a smooth continuous lumen for introduction of catheters and the like.

Figure 10:
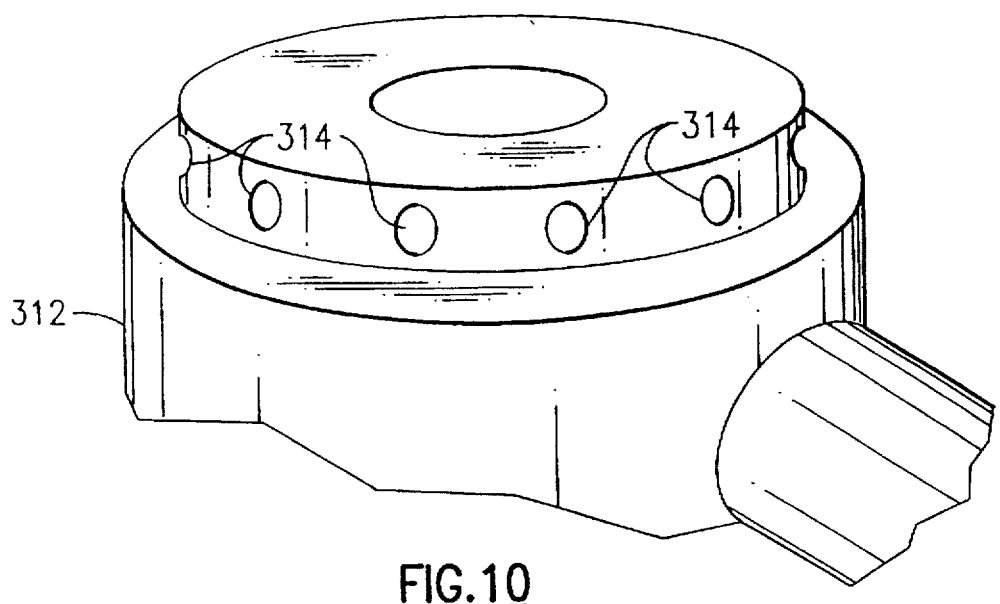
FIG. 10 is a perspective detail view of the main body showing optional detent indentions.
Figure 11A:
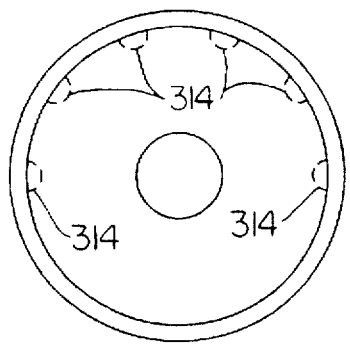
FIG. 11A is a top view of the main body of the introducer shown in FIG. 11.
Figure 11:
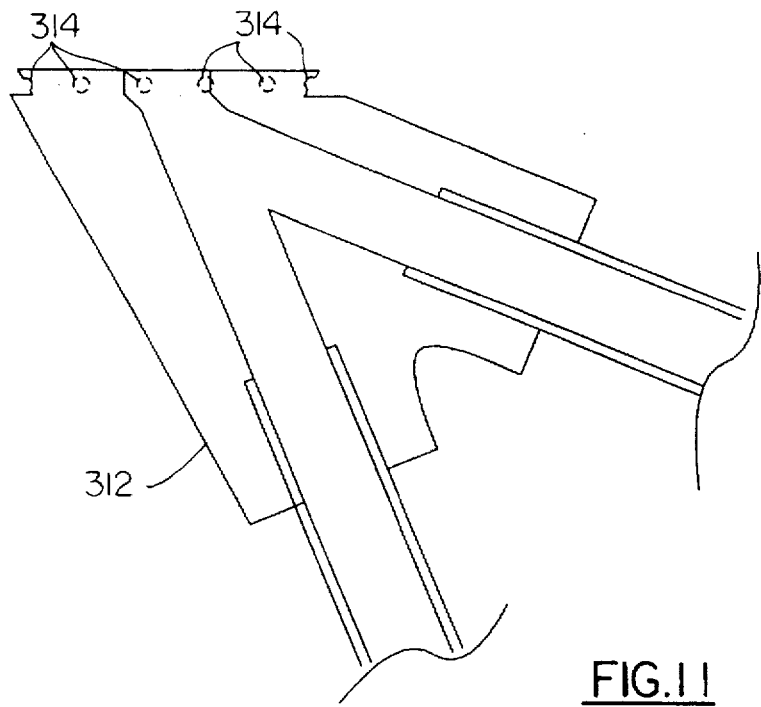
FIG. 11 is a side cutaway detail of the main body of the introducer of FIG. 6.

FIGS. 10–13 show a variation of the first preferred embodiment, which can also be incorporated into the alternative embodiment of the first preferred embodiment. FIGS. 10 and 11 show an introducer 300 with a main body 312 substantially as in the first two embodiments discussed hereinabove, with the incorporation of a series of semi-spherical indetentions 314 formed within the exterior sidewall 315. The indentations 314 are spaced about the sidewall 315 approximately every 30° for a total spacing of 180°. It is to be understood that other spacings are contemplated as being within the scope of the present invention.

Figure 12:
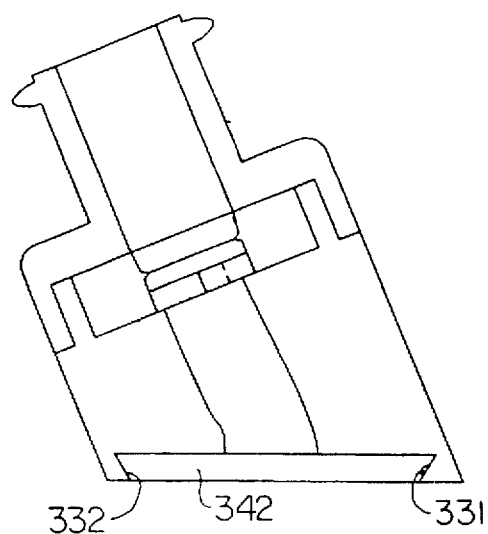
FIG. 12 is a side cutaway detail of the rotating section including a detent protrusion.
Figure 13:
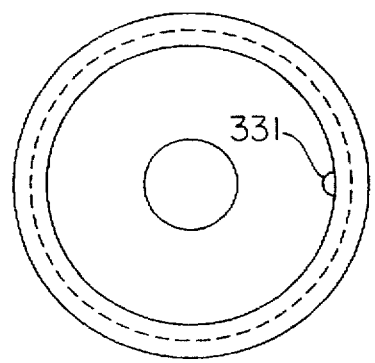
FIG. 13 is a bottom view of the rotating body of the introducer shown in FIG. 12.

FIGS. 12 and 13 show a rotating section 330 having a small semi-spherical protrusion 331 projecting inward from the inner beveled wall 332 of the annular recess 342. When the introducer 300 is assembled the rotating section 330 is snap fitted onto the main body 312, as described in detail hereinabove, with the protrusion 331 fitting within one of the indentations 314. In the unrotated position, the rotating section will be able to be rotatably journaled with detent stops every 30° for a total rotation of 180°. It is also possible for there to be a plurality of protrusions 331 spaced around the wall 332, if desired. It is desirable for the protrusion 331 to be rounded enough to engage the indentations 314 yet be able upon rotation to flex or compress slightly so as to move between the indentations 314. The indentations 314 permit more precise rotational journaling of the rotating section 330 with respect to the main body 312.

FIGS. 14–20 show a second preferred embodiment of the present invention including a pivoting "ball and socket" combination. An introducer 400 has a generally conically shaped main body 410 comprising a tapered exterior sidewall 412 having a rear sidewall 414, a front sidewall 416, the terms "rear" and "front" being relative terms used when viewing the device as in FIG. 14, where the sideport 417 (optional and shown facing the right side of the drawing), as described in detail hereinabove with respect to the first preferred embodiment, extends from the front of the introducer 400. Such terms are used herein for the sole convenience of the explanation of the construction and use of the invention. The rear sidewall 414 has a curved portion 418 extending upward, terminating at a top surface 420. The front sidewall 416 has a curved portion 422, terminating at a top surface 424. The rear curved portion 418 extends higher upward than does the curved portion 422, for reasons which will be discussed in greater detail hereinbelow, and both portions have a similar radius of curvature.

Figure 16:
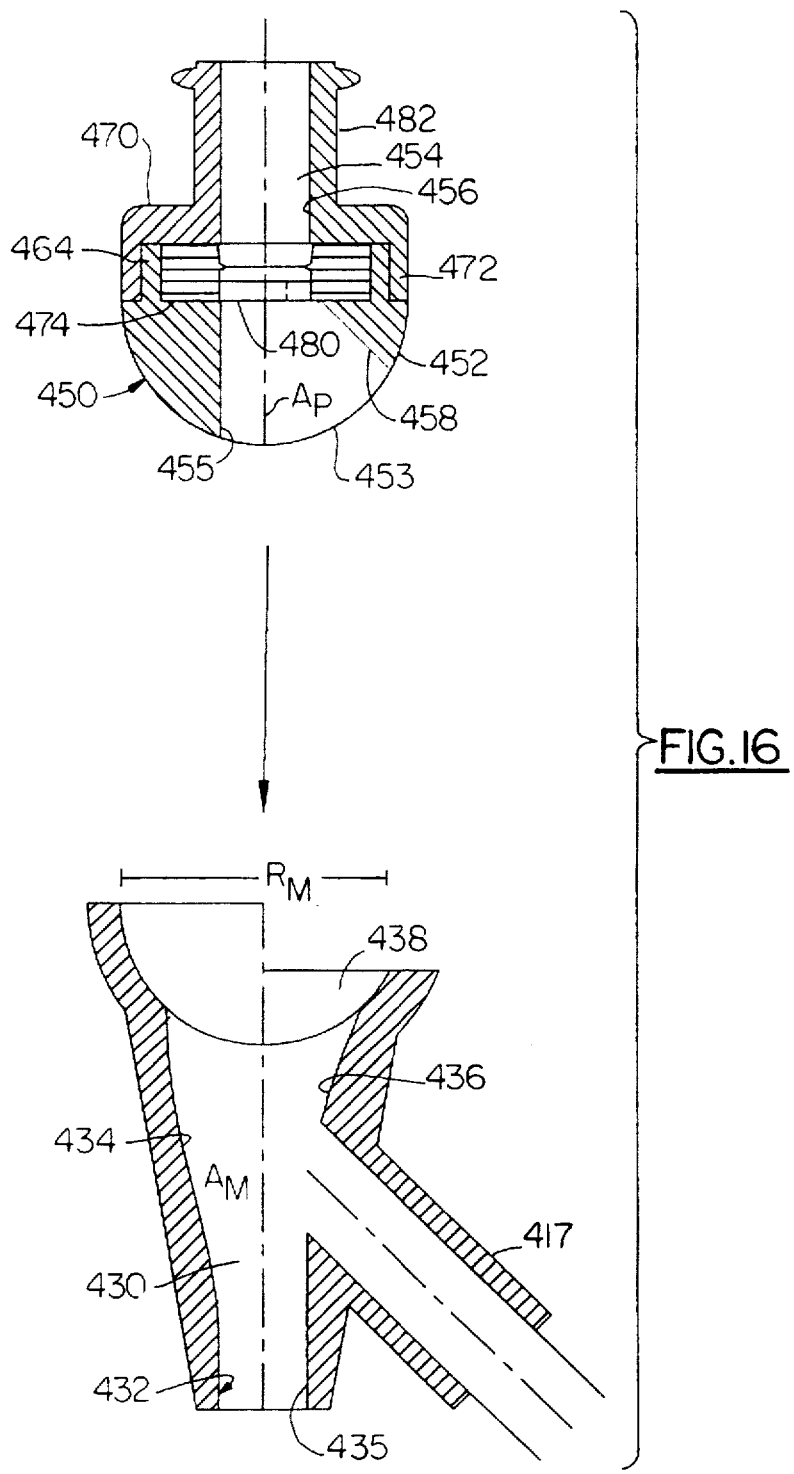
FIG. 16 is an expoded side cutaway view taken along lines 16—16 of FIG. 15.
Figure 17:
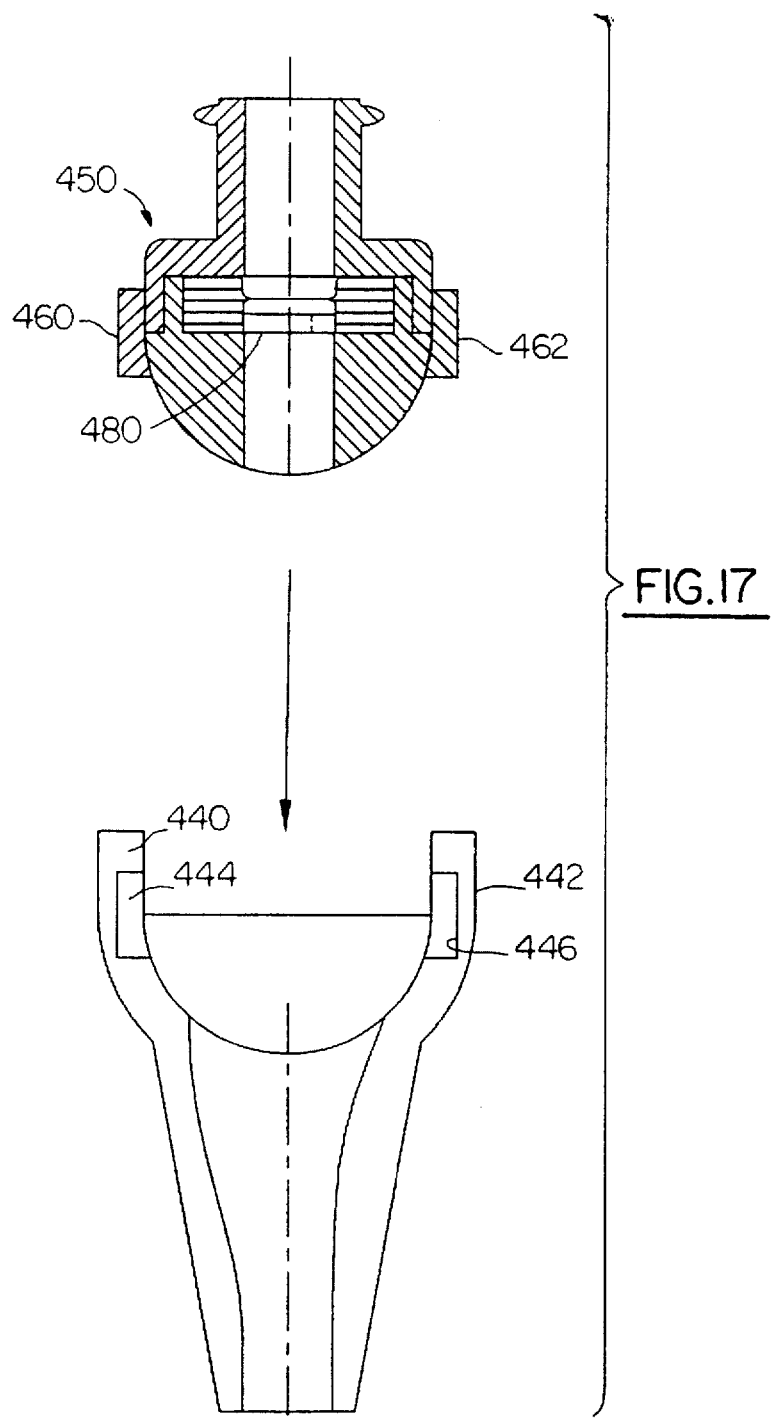
FIG. 17 is an exploded front cutaway view taken along lines 17—17 of FIG. 14.

The interior of the main body 410, as shown in FIGS. 16 and 17, has a lumen 430 defined therein having a first portion where the interior walls 432 are parallel, a rear upper portion 434 (see FIG. 16), which flares outward, a front lower portion 435 and a front upper portion 436, which also flares outward. A receptacle area 438 extending from the main body lumen 430 has a radius of curvature Rm. The main body lumen 430 has an axis defined as Am.

Figure 14:
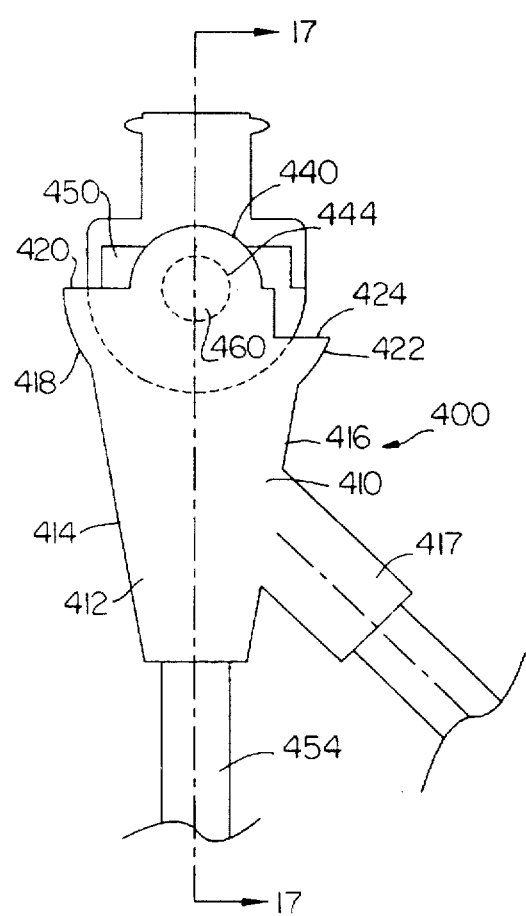
FIG. 14 is a left side view of a second preferred embodiment of the present invention.
Figure 15:
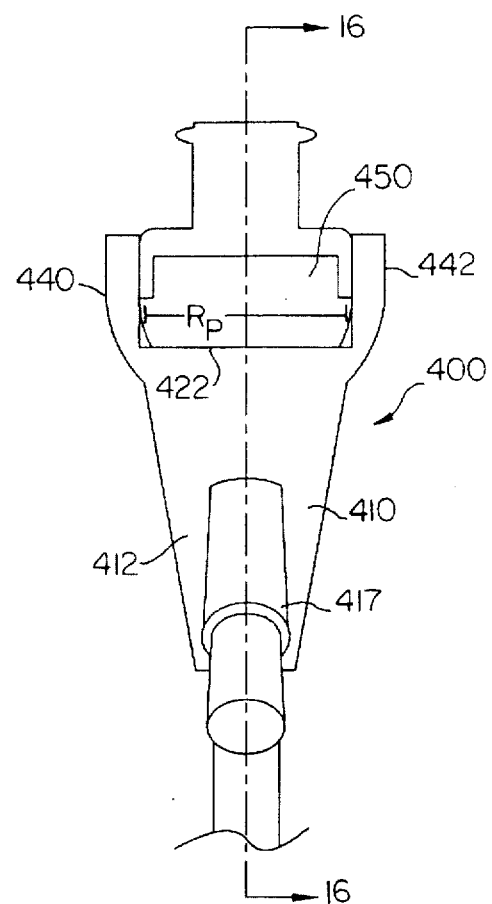
FIG. 15 is a front view of the second preferred embodiment.

FIGS. 15 and 17 show a left pivot bracket 440 extending from the sidewall 412 and a right pivot bracket 442 extending from the sidewall 412. FIGS. 14 and 17 show an aperture 444 defined in the left pivot bracket 440 and a corresponding aperture 446 defined in the right pivot bracket 442. A cannula 444, similar to cannula 80, extends from the main body 410 and is in fluid communication with the lumen 430.

A pivoting section 450 comprises an exterior wall 452, the lower area 453 of which is curved, having a radius of curvature Rp, where Rp is substantially the same as Rm, so that the pivoting section 450 can be pivotably received in the receptacle area 440 of the main body 410. The pivoting section 450 has a lumen 454 extending therethrough. The lumen 454 has an axis defined as Ap. The lumen 454 is defined by a rear wall 455 that is parallel to axis Ap, a front wall portion 456 that is parallel to axis Ap and a front wall lower portion 458 that is angled outward, with respect to the axis Ap, at approximately 45° forming a slot at the bottom of the rotating section slot width is the same as the lumen diameter. It is to be understood that the angle need not critical and that other angles are contemplated as being within the scope of the present invention. FIG. 17 shows the pivoting section 450 as having a left pintle 460 and a right pintle 462, each capable of being rotatably received within the corresponding bracket 440 and 442, respectively. The pivoting section 450 has an raised annular boss 464 extending upward.

An access port cap 470, similar to the access port cap 50 described hereinabove, has an annular shoulder 472 defining a recess 474. The access port cap 470 is fitted onto the pivoting section 450 as described hereinabove, with a valve 480 being compressively maintained within said recess 474 and in axial alignment with axis Ap. A luer fitting 482 is also associated with the access port cap 470, as described hereinabove. An optional stopcock assembly 490 can be included (not shown in the drawings), as described in detail hereinabove.

To assemble the introducer 400, the pivoting section 450 is fitted with the valve 480 and access port cap 470, as described hereinabove, and then fitted into the receptacle area 438. The pivot brackets 440 and 442 flex slightly to accommodate the pintles 460 and 462, which are fitted in the apertures 444 and 446, respectively. When assembled the axes Am and Ap are co-axial and the lumens 420 and 454 are co-axial.

Figure 18:
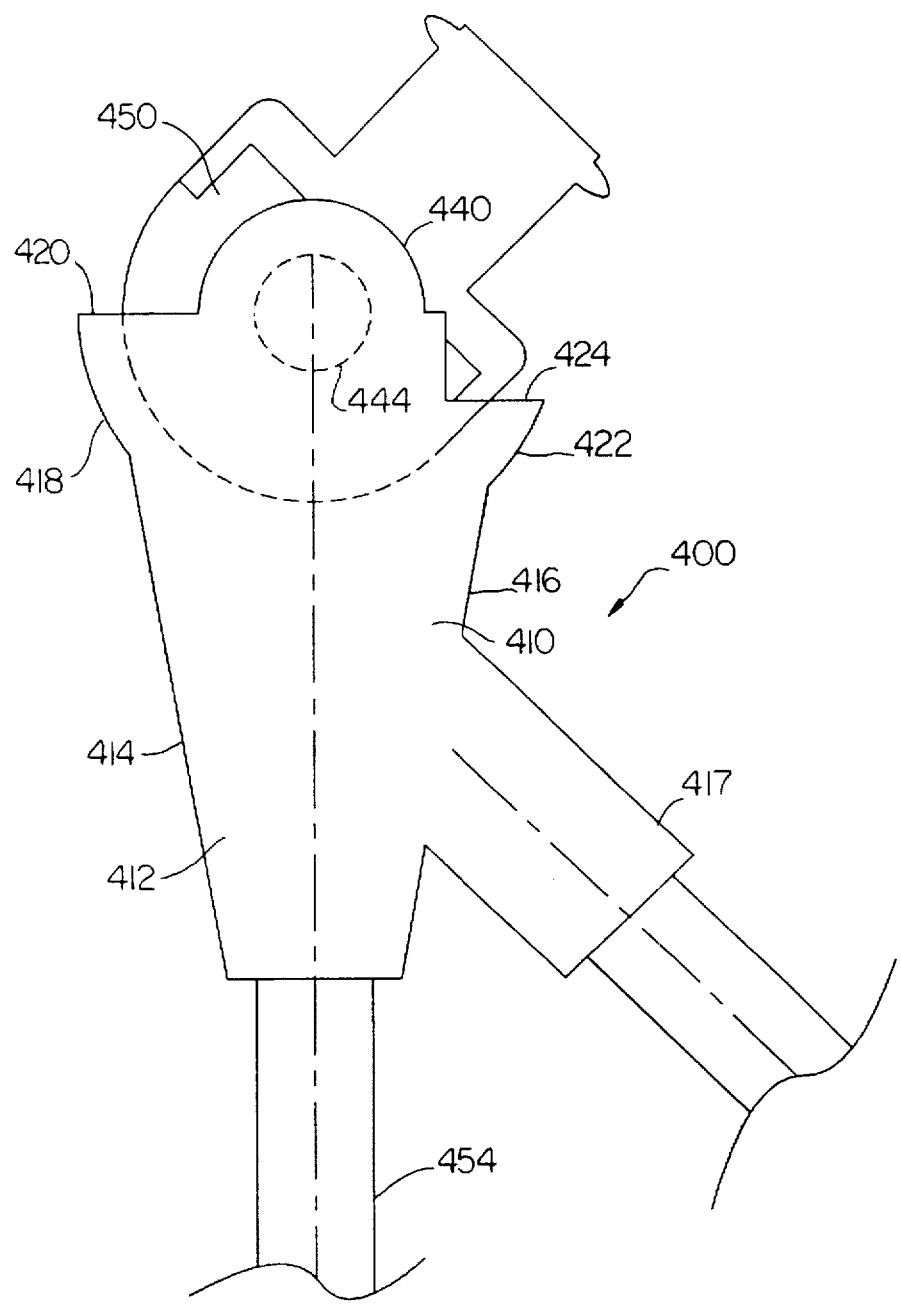
FIG. 18 is a left side view of a second preferred embodiment shown pivoted to about 45°.
Figure 19:
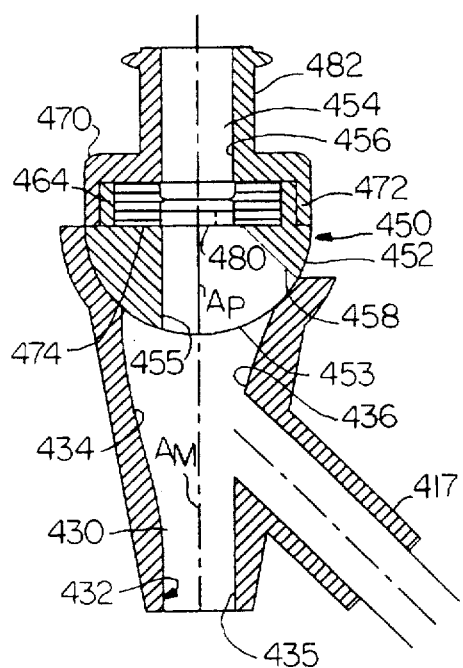
FIG. 19 is a left side cutaway view of the second preferred embodiment showing the introducer in the unpivoted 0° position.
Figure 20:
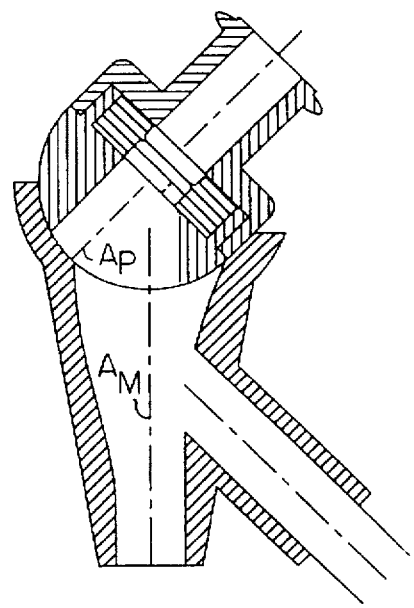
FIG. 20 is a left side cutaway view of the second preferred embodiment showing the introducer in the unpivoted 45° position.

FIGS. 14, 18, 19 and 20 illustrate the pivoting feature of this embodiment. In the base position, shown in FIGS. 14 and 19, the axes Am and Ap and lumens 420 and 454 are co-axial at 0°. The main body lumen rear wall lower portion 434 is in alignment with the pivoting section lumen rear wall 455 and the main body lumen front wall lower portion 435 is in alignment with the pivoting section lumen front wall upper portion 456, such that a clear and open path is available for insertion of catheters or other objects through the introducer. A user can manually pivot the pivoting section 450, which can optionally include knurls or other gripping surfaces (not shown) similar to those described hereinabove, from the 0° position to a maximum of approximately 45°, as shown in FIGS. 18 and 20. FIG. 20 shows the orientation of the lumens 430 and 454 whereby axis Ap is now pivoted 45° with respect to Am. The pivoting section lumen front wall lower portion 435 is now parallel and aligned with the main body lumen front wall lower portion 435, maintaining a clear open passageway for objects within the introducer 400. Additionally, the increased height of the sidewall rear curved portion 418 maintains a fluid tight seal with the pivoting section exterior wall 452 both in the 0° and at all pivoting angles. The shorter sidewall front curved portion 418 permits movement of the pivoting section 450, in general, and the annular shoulder 472 area, in specific, while restricting the pivoting section to a final rotation of a maximum of approximately 45°.

Figure 21:
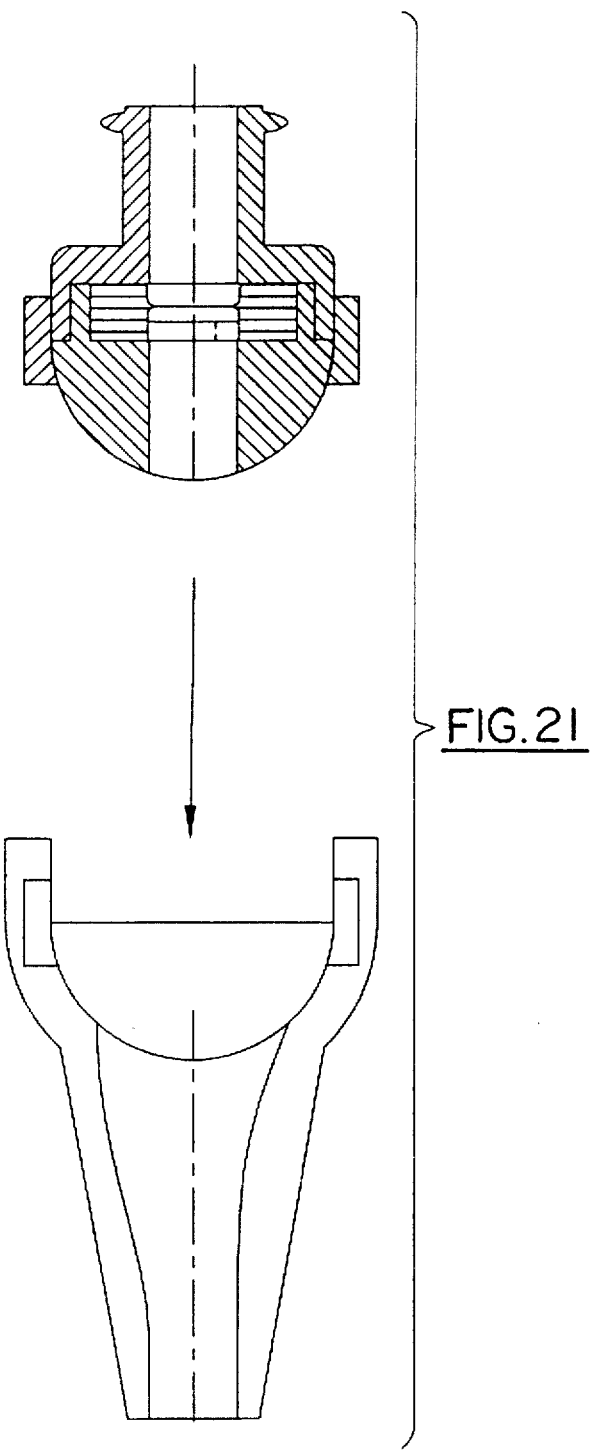
FIG. 21 is an exploded front cutaway view of a variant on the second preferred embodiment showing the indentation and protrusion.
Figure 22:
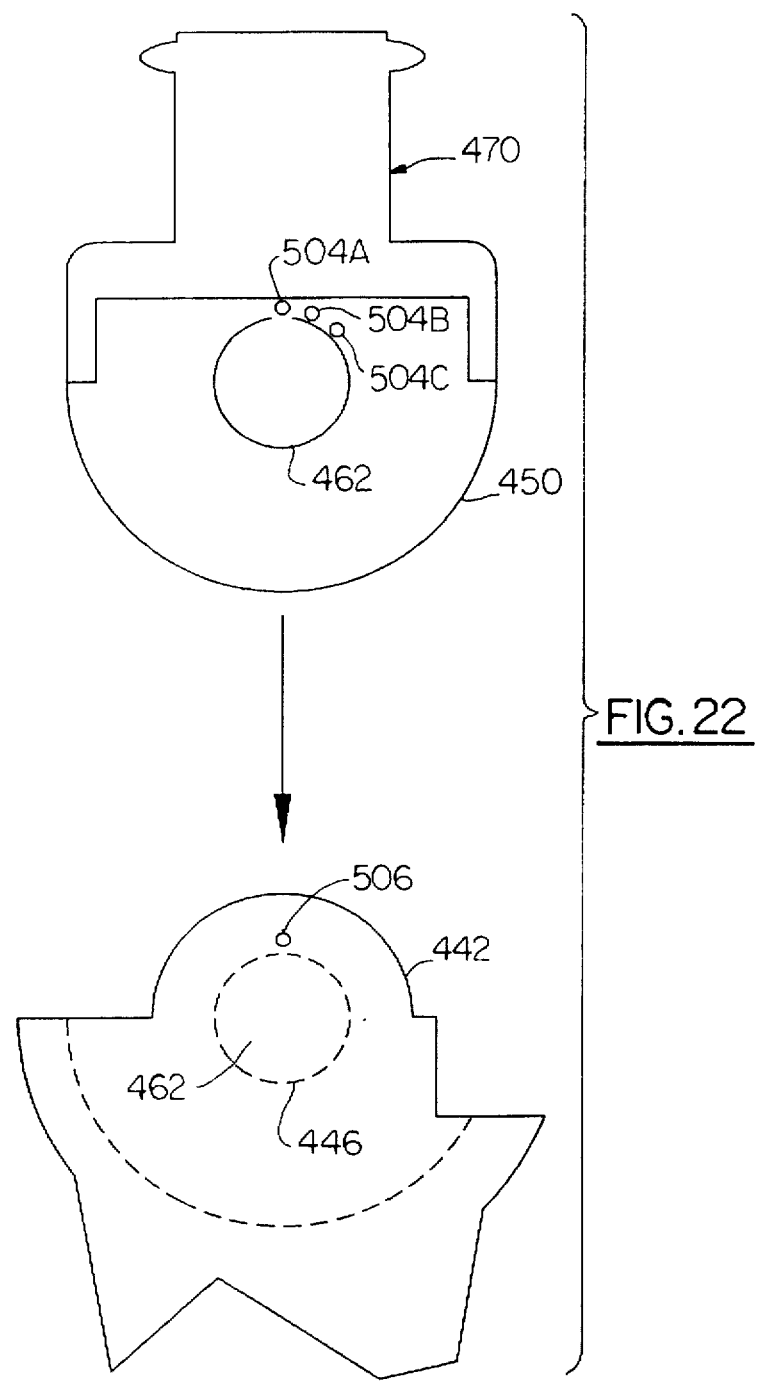
FIG. 22 is an exploded left side cutaway view of the embodiment shown in FIG. 21.
Figure 23:
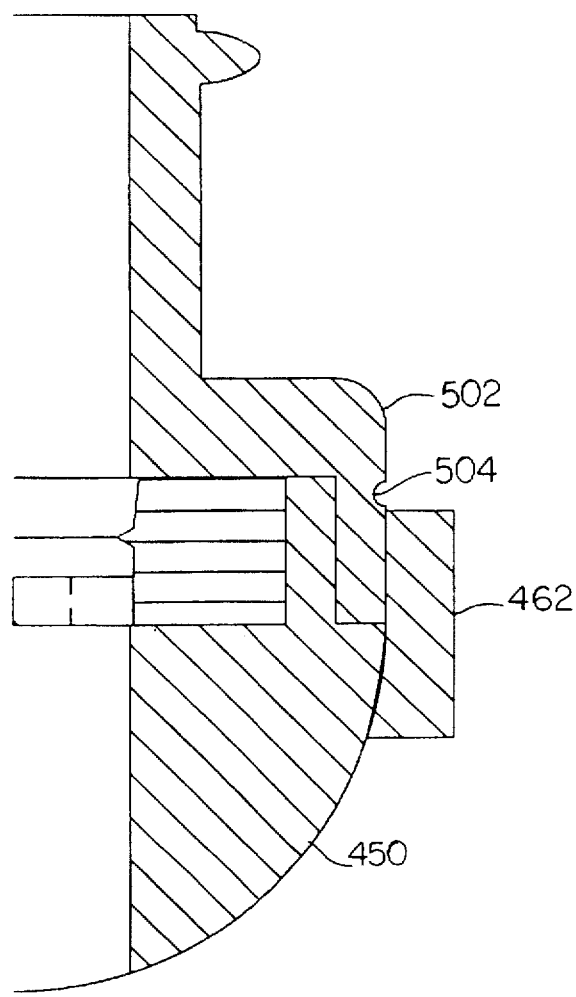
FIG. 23 is a partial cutaway front detail view of the pivoting section of the second embodiment shown in FIG. 21.
Figure 24:
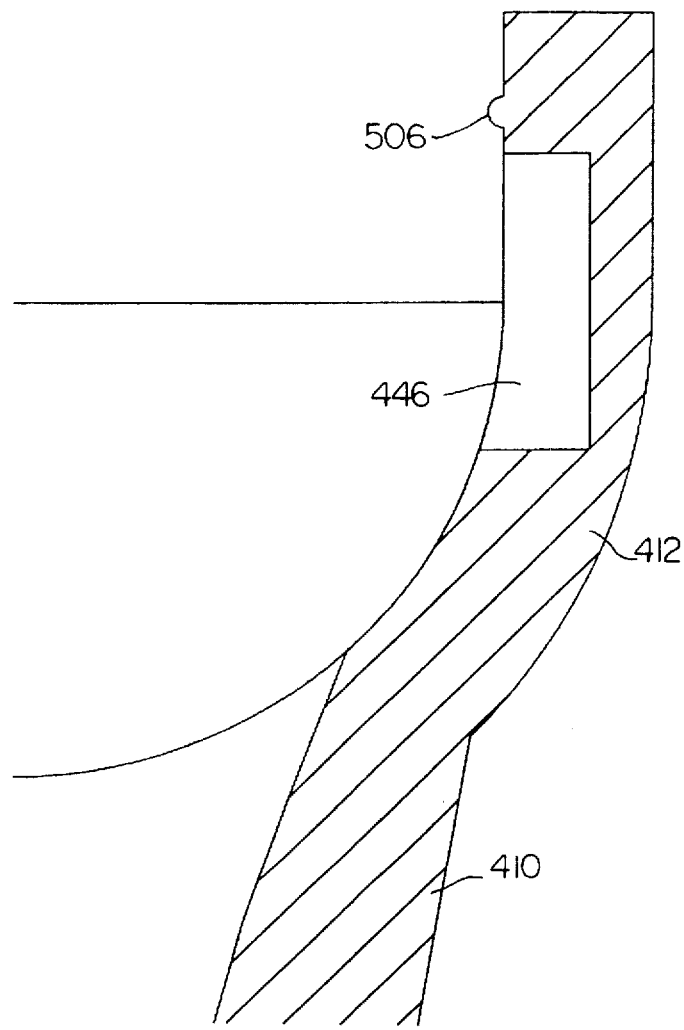
FIG. 24 is a partial cutaway front detail view of the main body of the second embodiment shown in FIG. 21.

FIGS. 21–24 show an optional addition to the second preferred embodiment described hereinabove, in which the right side 502 of the pivoting section exterior wall right pintle 462 has a series of indentations 504A–C (504 collectively), preferably three indentations spaced 15° apart, spaced around the light pintle 462, as shown in FIGS. 21–23. It is to be understood that other numbers, spacing and positioning of the indentations 504 are contemplated as being within the scope of the present invention. The right pivot bracket 442 has a semi-spherical protrusion 506 extending therefrom, just above the right aperture 446, as shown in FIGS. 22 and 24. When the main body 410 and pivoting section 450 are mated, the protrusion 506 fits within one of the indentations 504A. When the pivoting section is pivoted, the indentations 504 journal and the right bracket 442 flexes slightly causing the protrusion 506 to be removed from the indentation 504A and register with the next indentation 504B, and then to indentation 504C. Thus, the pivoting section 450 can rotate with detent stops from approximately 0° to approximately 45°. An advantage of using detents is that it makes positioning of the introducer easier and provides a gentle means of maintaining the angle of the pivoting section until the user repositions the introducer; however, in the event a patient inadvertently moves, such as during a coughing spell, seizure or other traumatic movement, the introducer 400 can pivot to accommodate some of this movement to reduce possible kinking of a catheter or the like or trauma to the skin or vessel.

While the invention has been described in connection with certain preferred embodiments, it is not intended to limit the scope of the invention to the particular forms set forth, but, on the contrary, it is intended to cover such alternatives, modifications, and equivalents as may be included within the spirit and scope of the invention as defined by the appended claims.

What is claimed is:

1. A hemostatic sheath introducer, comprising:
   a) a generally cylindrically shaped main body having a main axis and comprising
      i) an exterior sidewall,
      ii) a top surface having an annular boss extending therefrom, said boss terminating in a flange for mating with an annular recessed portion, said top surface and boss being beveled at an acute angle with respect to said sidewall,
      iii) a bottom end,
      iv) a first lumen extending through said main body, said boss and said bottom end;
   b) a rotating section comprising
      i) a generally cylindrically shaped body having an exterior dimension generally similar to said main body sidewall and a lumen extending therethrough,
      ii) a lower end having an annular recessed portion defined therein for mating with said main body boss and flange, said lower end having a lower surface being beveled at an acute angle with respect to said rotating section,
      iii) an upper end having an upper surface being generally perpendicular to said main body sidewall; said rotating section maintaining a fluid sealed relationship with said main body and maintaining said lumen in fluid communication with said first lumen when said rotating section is rotationally journaled with respect to said main body;
   c) an access port being attachable to said rotating section and comprising
      i) a luer fitting portion having an interior luer taper and an exterior luer fitting,
      ii) a sealing portion having an exterior dimension generally similar to the exterior dimension of said rotating section upper end, and a recessed portion,
      iii) an opening therethrough;
   d) an elastomeric valve having an opening defined therein adapted for receiving an elongated member in a slidingly sealable relationship, said valve being receivable within said recessed portion of said access port and maintained in place thereby; and,
   e) a cannula extending from the bottom end of said main body and comprising
      i) a proximal end extending from said main body bottom,
      ii) a distal end, and
      iii) a lumen extending therethrough being in fluid communication with said first lumen said cannula being offset from the center axis of said main body.

2. The sheath introducer of claim 1, further comprising a sideport extending laterally outward from said main body, said side port comprising a boss, a second lumen defined within said boss and in fluid communication with said first lumen and a tube extending outward from said boss.

3. The sheath introducer of claim 2, wherein said tube is connected to a stopcock.

4. The sheath introducer of claim 2, wherein said sideport boss is angled downward in the direction of said cannula.

5. The sheath introducer of claim 2, wherein said sideport is rotationally offset from said access port.

6. The sheath introducer of claim 5, wherein said angle of said boss is offset approximately 45°.

7. The sheath introducer of claim 2, further comprising a plurality of detents disposed on said main body top surface and said rotating section bottom surface.

8. The sheath introducer of claim 1, wherein a portion of said cannula is tapered.

9. The sheath introducer of claim 3, wherein the distal end of said cannula is tapered.

10. The sheath introducer of claim 1, wherein said valve opening is a Y-shaped slit in cross-section such that said elastomeric valve continues to maintain a fluid tight seal when a tube is slidingly inserted therein while permitting movement of said tube.

11. The sheath introducer of claim 1, said main body, rotating section, access port cap and cannula are made of a plastic material.

12. The sheath introducer of claim 1, wherein said valve opening has an annular inwardly protruding flange capable of forming a seal when an elongated tube member is, slidingly inserted into said opening.

13. The sheath introducer of claim 12, wherein said elongated tube member is selected from the group consisting of a catheter, a stent, a shunt and a needle.

14. The sheath introducer of claim 1, wherein said rotating section is angled at approximately 45° with respect to said main body.

15. The sheath introducer of claim 1, wherein said access port has an exterior luer thread.

16. The sheath introducer of claim 1, further comprising a dilator comprising a body and a tube, said tube being slidingly receivable within said rotating section, said main body and said cannula.

17. The sheath introducer of claim 1, wherein said rotating section can be rotatingly journaled with respect to said main body from an angle of about 0° to about 90° while maintaining a fluid sealed relationship.

18. The sheath introducer of claim 1, wherein said access port sealing portion is fixedly attached to said upper end of said rotating portion.

19. The sheath introducer of claim 18, wherein said sealing is achieved by a method selected from the group consisting of ultraviolet light curing, gluing, solvent bonding, and sonic welding.

20. The sheath introducer of claim 19, wherein said valve is maintained in a compressed state between said access port and said rotating section.

21. The sheath introducer of claim 1, wherein said upper end surface of said rotating section has an annular rim extending therefrom and said sealing portion of said access port has a recessed portion capable of matingly engaging said annular rim so as to form a friction fit joint.

22. The sheath introducer of claim 1, wherein said main body top annular boss further comprises a series of circumferentially spaced indentations capable of passing over a plurality of ridges circumferentially spaced within said annular groove of said rotating section such that said rotating section can rotate with respect to said main body in a detent manner.

23. A hemostatic sheath introducer, comprising:
 a) a generally cylindrically shaped main body having a main axis and comprising
  i) an exterior sidewall,
  ii) a top surface having an annular boss extending therefrom, said boss terminating in a flange for mating with an annular recessed portion, said top surface and boss being beveled at an acute angle with respect to said sidewall,
  iii) a bottom end,
  iv) a first lumen extending through said main body, said boss and said bottom end, said first lumen having an angled portion proximate to said boss so that said first lumen angled portion is perpendicular to said boss;
 b) a rotating section comprising
  i) a generally cylindrically shaped body having an exterior dimension generally similar to said main body sidewall and a second lumen extending therethrough,
  ii) a lower end having an annular recessed portion defined therein for mating with said main body boss and flange, said lower end having a lower surface being beveled at an acute angle with respect to said rotating section,
  iii) an upper end having an upper surface being generally perpendicular to said main body sidewall; said rotating section maintaining a fluid sealed relationship with said main body and maintaining said lumen in fluid communication with said first lumen when said rotating section is rotationally journaled with respect to said main body, and said second lumen having an angled portion proximate to said annular recessed portion so that said second lumen angled portion is perpendicular to said annular recessed portion;
 c) an access port being attachable to said rotating section and comprising
  i) a luer fitting portion having an interior luer taper and an exterior luer fitting,
  ii) a sealing portion having an exterior dimension generally similar to the exterior dimension of said rotating section upper end, and a recessed portion,
  iii) an opening therethrough;
 d) an elastomeric valve having an opening defined therein adapted for receiving an elongated member in a slidingly sealable relationship, said valve being receivable within said recessed portion of said access port and maintained in place thereby; and,
 e) a cannula extending from the bottom end of said main body and comprising
  i) a proximal end extending from said main body bottom,
  ii) a distal end, and
  iii) a lumen extending therethrough being in fluid communication with said first lumen said cannula being offset from the center axis of said main body.

24. A hemostatic sheath introducer, comprising:
 a) a generally cylindrically shaped main body having a main axis and comprising
  i) an exterior sidewall, having a front portion, a rear portion, a left side portion and a right side portion, said rear portion extending upward higher than said front portion, said exterior sidewall having a taper thereto,
  ii) a left bracket extending from said left side portion, said left bracket having an aperture defined therein,
  iii) a right bracket extending from said right side portion, said right bracket having an aperture defined therein,
  iv) a bottom end, and
  v) a first lumen extending therethrough, said lumen having
   a) a lower parallel wall portion,
   b) a middle reverse tapered portion,
   c) an upper curved portion, said curve having a radius of curvature Rm;
 b) a pivoting section comprising
  i) an exterior wall having front, rear, left side and right side portions, a lower portion which is curved and having a radius of curvature Rp, said radius Rp being substantially similar to said radius Rm, ii) an upper surface, iii) a second lumen defined therein, said second lumen having
- a) a substantially straight rear wall,
- b) a front wall that is angled outward toward said exterior wall, iv) a left pintle extending from said pivoting section left side portion, v) a right pintle extending from said pivoting section right side portion, said left pintle being pivotably receivable within said left bracket aperture and said right pintle being pivotably receivable within said right bracket aperture;

c) an access port being attachable to said rotating section and comprising
  i) a luer fitting portion having an interior luer taper defining a third lumen and an exterior luer fitting,
  ii) a sealing portion comprising an annular shoulder portion having an exterior dimension generally similar to the exterior dimension of said pivoting section upper end, and a recessed portion;

d) an elastomeric valve having an opening defined therein adapted for receiving an elongated member in a slidingly sealable relationship, said valve being receivable within said recessed portion of said access port and maintained in place thereby; and, e) a cannula extending from the bottom end of said main body and comprising
  i) a proximal end extending from said main body bottom,
  ii) a distal end, and
  iii) a fourth lumen extending therethrough being in fluid communication with said first lumen,
  whereby said pivoting section can pivot on said left and right pintles within said left and right brackets, respectively, while maintaining an open passageway through said introducer.

25. A sheath introducer, comprising:

a) a generally cylindrically shaped main body having a main axis and comprising
  i) an exterior sidewall,
  ii) a top surface having an annular boss extending therefrom, said top surface and boss being beveled at an acute angle with respect to said sidewall,
  iii) a bottom end,
  iv) a first lumen extending through said main body, said boss and said bottom end;

b) a rotating section comprising
  i) a generally cylindrically shaped body having an exterior dimension generally similar to said main body sidewall and a lumen extending therethrough, said lumen being in fluid communication with said first lumen,
  ii) a lower end having an annular recessed portion defined therein for mating with said main body boss, said lower end having a lower surface being beveled at an acute angle with respect to said rotating section.
  iii) an upper end having an upper surface being generally perpendicular to said main body sidewall; said rotating section maintaining a fluid sealed relationship with said main body and maintaining said lumen in fluid communication with said first lumen when said rotating section is rotationally journaled with respect to said main body;

c) an access port being attachable to said rotating section and comprising
  i) a sealing portion having an exterior dimension generally similar to the exterior dimension of said rotating section upper end, and a recessed portion,
  ii) an opening therethrough;

d) an elastomeric valve having an opening defined therein adapted for receiving an elongated member in a slidingly sealable relationship, said valve being receivable within said recessed portion of said access port and maintained in place thereby; and, e) a cannula extending from the bottom end of said main body and comprising
  i) a proximal end extending from said main body bottom,
  ii) a distal end, and
  iii) a lumen extending therethrough being in fluid communication with said first lumen said cannula being offset from the center axis of said main body.

26. A sheath introducer, comprising:

a) a generally cylindrically shaped main body having a main axis and comprising
  i) an exterior sidewall,
  ii) a top surface having an annular boss extending therefrom, said top surface and boss being beveled at an acute angle with respect to said sidewall,
  iii) a bottom end,
  iv) a first lumen extending through said main body, said boss and said bottom end, said first lumen having an angled portion proximate to said boss so that said first lumen angled portion is perpendicular to said boss;

b) a rotating section comprising
  i) a generally cylindrically shaped body having an exterior dimension generally similar to said main body sidewall and a second lumen extending therethrough, said lumen being in fluid communication with said first lumen,
  ii) a lower end having an annular recessed portion defined therein for mating with said main body boss, said lower end having a lower surface being beveled at an acute angle with respect to said rotating section.
  iii) an upper end having an upper surface being generally perpendicular to said main body sidewall; said rotating section maintaining a fluid sealed relationship with said main body and maintaining said lumen in fluid communication with said first lumen when said rotating section is rotationally journaled with respect to said main body, and
  said second lumen having an angled portion proximate to said annular recessed portion so that said second lumen angled portion is perpendicular to said annular recessed portion;

c) an access port being attachable to said rotating section and comprising
  i) a sealing portion having an exterior dimension generally similar to the exterior dimension of said rotating section upper end, and a recessed portion,
  ii) an opening therethrough;

d) an elastomeric valve having an opening defined therein adapted for receiving an elongated member in a slidingly sealable relationship, said valve being receivable within said recessed portion of said access port and maintained in place thereby; and, e) a cannula extending from the bottom end of said main body and comprising
  i) a proximal end extending from said main body bottom, ii) a distal end, and iii) a lumen extending therethrough being in fluid communication with said first lumen said cannula being offset from the center of axis of said main body.

27. A sheath introducer, comprising:

a) a generally cylindrically shaped main body having a main axis and comprising i) an exterior sidewall, having a front portion, a rear portion, a left side portion and a right side portion, ii) a left bracket extending from said left side portion, said left bracket having, an aperture defined therein, iii) a right bracket extending from said right side portion, said right bracket having an aperture defined therein, iv) a bottom end, and v) a first lumen extending therethrough, said lumen having an upper curved portion, said curve having a radius of curvature Rm;

b) a pivoting section comprising i) an exterior wall having front, rear, left side and right side portions, a lower portion which is curved and having a radius of curvature Rp, said radius Rp being substantially similar to said radius Rm, ii) an upper surface, iii) a second lumen defined therein, said second lumen having a) a substantially straight real wall, b) a front wall that is angled outward toward said exterior wall, iv) a left pintle extending from said pivoting section left side portion, v) a right pintle extending from said pivoting section right side portion, said left pintle being pivotably receivable within said left bracket aperture and said right pintle being pivotably receivable within said right bracket aperture;

c) an access port being attachable to said rotating section and comprising i) a third lumen, ii) a sealing portion comprising an annular shoulder portion having an exterior dimension generally similar to the exterior dimension of said pivoting section upper end, and a recessed portion;

d) an elastomeric valve having an opening defined therein adapted for receiving an elongated member in a slidingly sealable relationship, said valve being receivable within said recessed portion of said access port and maintained in place thereby; and, e) a cannula extending from the bottom end of said main body and comprising i) a proximal end extending from said main body bottom, ii) a distal end, and iii) a fourth lumen extending therethrough being in fluid communication with said first lumen, whereby said pivoting section can pivot on said left and right pintles within said left and right brackets, respectively, while maintaining an open passageway through said introducer.

* * * * *